United States Patent [19]

Kurze et al.

[11] Patent Number: 4,820,388
[45] Date of Patent: Apr. 11, 1989

[54] POLYALKYLENE GLYCOL NAPHTHYL-3-SULFOPROPYL DIETHER COMPOUNDS AND THEIR SALTS, PROCESS FOR PREPARING SAME AND ELECTROPLATING BATHS CONTAINING SAME

[75] Inventors: Werner Kurze, Neuhofen; Klaus-Peter Klos, Trebur, both of Fed. Rep. of Germany

[73] Assignees: Raschig AG, Ludwigshafen; Elektro-Brite GmbH & Co. KG, Trebur, both of Fed. Rep. of Germany; a part interest

[21] Appl. No.: 205,631

[22] Filed: Jun. 13, 1988

[30] Foreign Application Priority Data

Jul. 9, 1987 [DE] Fed. Rep. of Germany ....... 3722778

[51] Int. Cl.$^4$ ................ C07C 143/30; C07C 143/32; C07C 143/34
[52] U.S. Cl. .............................. 204/44.2; 106/1.25; 204/43.1; 204/44; 204/44.4; 204/44.5; 204/45.1; 204/46.1; 204/49; 204/52.1; 204/54.1; 204/55.1; 260/512 C
[58] Field of Search ................ 260/512 C; 204/43.1, 204/44.2, 44.3, 44.4, 44.5, 44.6, 44.7, 44, 45.1, 45.5, 46.1, 47, 47.5, 48, 49, 50.1, 50.3, 51, 52.1, 52.5, 53, 54.1, 54.5, 55.1, 55.3, 55.5; 106/1.25

[56] References Cited

U.S. PATENT DOCUMENTS 4,153,575  5/1979  Kalfoglou et al. .......... 260/512 CX

Primary Examiner—G. L. Kaplan
Attorney, Agent, or Firm—Collard, Roe & Galgano

[57] ABSTRACT

Novel Polyalkylenglycol naphthyl-3-sulfopropyl diethers and salts thereof of the formula

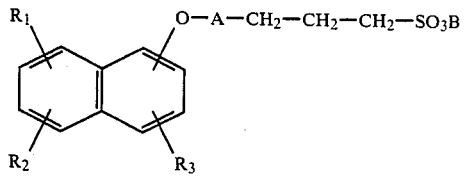

($R_1$–$R_3$=H, $C_pH_{2p-1}$; p=1—4, A=$(PO)_m$—$(EO)_n$—, $(EO)_n$—$(PO)_m$,—$(EO)_n$ EO=ethylenoxide residue, PO=propylenoxide residue, m=0—15, n—1—40, A=H, alkali metal, earth alkali metal, $NR_5R_6R_7R_8$ wherein $R_5$–$R_8$=H, $C_1$–$C_4$—alkyl, aryl, aralkyl) are prepared by reacting the corresponding polyalkylene glycol naphthyl either with propane-1.3-sultone. The compounds are surfactants in particular in electroplating baths for precipitation Zn, Sn, Cu, Ag, Ni and alloys thereof.

7 Claims, No Drawings

POLYALKYLENE GLYCOL NAPHTHYL-3-SULFOPROPYL DIETHER COMPOUNDS AND THEIR SALTS, PROCESS FOR PREPARING SAME AND ELECTROPLATING BATHS CONTAINING SAME

The invention relates to novel Polyalkylene glycol naphthyl-3-sulfopropyl diethers and salts thereof as well as a process for preparing these compounds and electroplating baths containing these compounds as surfactants.

It is known to use ethoxylated $\beta$-naphthol as surfactant when depositing metals from electroplating baths. These compounds are in particular suited to keep the chemical brightenners in solution and to act as wetting agents for the cathode surface and to prevent the formation of the so-called hydrogen pores which occur when hydrogen is fixed at the cathodic metal surface together with the metal to be deposited such as zinc, cadmium, copper, silver and the like. However, the solubility of these non-ionic compounds is strongly dependant from pH, from the salt concentration, from the temperature and from the chain length of the molecules. The compounds are not suited for high perfomance electroplating baths which are used at high current densities up to about 150 A/dm$^2$ and increased temperature up to about 79° C.

Sulfated derivatives of the known compounds are known from German Patent Publication No. 34 32 956. However, these compounds are either not resistant to high hydrolysis or are less suited as brightening agents.

It has now been found that the disadvantages of the prior art compounds are eliminated when using novel compounds which are reaction products of similar alkoxylated naphthols with propane-1,3-sultone. A reaction product of $\beta$-naphthol with propane-1,3-sultone is known from a German patent publication No. 19 63 818; this compound however is a drug and has so far not been used in electroplating baths.

The polyalkylene glycol naphthyl-3-sulfopropyl diethers of the invention have the general formula

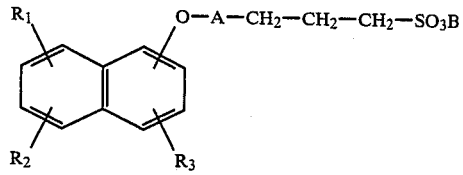   (I.)

wherein $R_1$, $R_2$ and $R_3$ are hydrogen or a lower alkyl group $C_pH_{2p+1}$ wherein p is 1 to 4 and A is a group —(PO)$_m$—(EO)$_n$ or —(EO)$_n$—(PO)$_m$— or —(EO)(PO)$_n$— wherein EO is a group —CH$_2$CH$_3$—O— and PO is a group

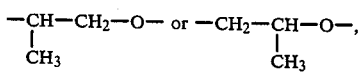

m means an integer of 0 to 15 and n is an integer of 1 to 40 and B is hydrogen, an alkali metal, an earth alkali metal or an ammonium cation NR$_4$R$_5$R$_6$R$_7$ wherein R$_4$ to R$_7$ are hydrogen, C$_1$–C$_4$—alkyl, aryl or aralkyl.

Compounds of the formula I are prepared by alkoxylating a corresponding $\alpha$- or $\beta$-naphthol with ethylene oxide and/or propyleneoxide in a known manner and reacting the compound of formula II

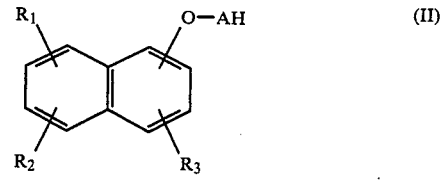   (II)

with propane-1,3-sultone in the presence of alkali hydroxides, earth alkali hydroxides or quaternary ammonium hydroxides NR$_4$R$_5$R$_6$R$_7$OH in which R$_4$ to R$_7$ have the meaning indicated above with the exception of hydrogen whereafter optionally the cation B is replaced by hydrogen in a known manner.

The exchange of cation B against hydrogen is carried out e.g. by ion exchange resins. Compounds with B=NR$_4$R$_5$R$_6$R$_7$ wherein R$_4$, R$_5$, R$_6$ and R$_7$ are not or partly hydrogen are prepared in a known way by neutralizing of the acids.

The reaction of the compound of formula II with propane-1,3-sultone is carried at temperatures in the range of 0° to 100° C. depending from the chain length of the alkoxy group and of the desired reaction speed.

Preferred are compounds wherein $R_1$, $R_2$ and $R_3$ are hydrogen and CH$_3$ and n is 2 to 10 and m is 1 to 5 and B is potassium or sodium. In these cases a reaction temperature with propane-1,3-sultone of 35° to 50° C. is preferred.

The use of the compounds of the invention as surfactant in electroplating baths is also possible with compounds having m=0. Particularly preferred are compounds wherein m=1 to 5 and n=2 to 24, in particular 6 to 10. Useful for the galvanotechnic purposes are not only derivatives of $\alpha$- and $\beta$-naphtol but also substituted derivatives thereof wherein 1 to 3 substituents which may be equal or different, in particular methyl, ethyl, propyl, isopropyl, butyl and isobutyl may be present. The presence of such substituents is not disadvantageous for the stability of such compounds.

The fact whether B is a proton or one of the alkali metals such as sodium or potassium or one of the earth alkali metals such as calcium, or an amine or ammonium cation is not particularly critical since in electroplating baths these compounds disintegrate in free ions.

An ammonium cation such as of the formula NR$_4$R$_5$R$_6$R$_7$ with R$_4$ to R$_7$ being hydrogen, a C$_1$–C$_4$ lower alkyl group, aryl group or aralkyl group are suitable.

The amounts of the compounds of the invention to be used in electroplating baths are 0.01 to 20 g/l. Such baths are preferred which are used for the deposition of zinc and its alloys, nickel, copper and its alloys, tin and its alloys, as well as silver. Also for electroless plating baths such as chromatizing baths the compounds are suited.

The compounds of the invention have no cloud point and are very easily dispersible in grease and oil. Therefore they are useful as surfactants in degreasing baths in concentrations of 0.1 to 100 g/l.

The use of the compounds of the invention in electroplating baths surpringly does not passivate the surface of the cathodes. The action corresponds to that of blends of non-ionic and ionic surfactants but in addition bright deposits in a large range of current densities with good, up to very good, ductility are produced. With increased temperature and current density in high performance baths the compounds are very stable. Further foaming occurs to only a very limited degree. Therefore the compounds can be used in electroplating baths under aeration e.g. for depositing nickel.

The invention is illustrated by the following examples.

EXAMPLE 1

Production of the dipotassium salt of polyethylene glycol-(2-naphthyl)-(3-sulfo-propyl) diether:

To 0.5 moles of 2-naphthol ethoxylate (n=6-24) there are added at 40 to 50° C. 0.505 moles of potassium hydroxide (calculated on pure KOH without potash and other impurities) with stirring within 0.5 hours whereby a slight exothermic reaction occurs which may necessitate cooling. Thereafter at the same conditions 0.5 moles of molten propane-1,3-sultone (melt temperature 40° to 50° C.) are added within 1 hour with cooling. For a complete reaction the blend is further agitated for 3 hours at 40° to 50° C. There is obtained 95 to 105% of a light to dark brown viscous liquid (n=6-15) or waxy (n=24) product with the following properties:

| | | |
|---|---|---|
| Content of compound: | 75-87% | according to two phase titration |
| Water | 2-5% | (Karl-Fischer-Titration |
| pH | 9-12 | (10% in water) |

The products are soluble in water and 10% aqueous sulfuric acid.

The following examples show the use of the compounds as surfactants in electroplating baths:

EXAMPLE 2 a. Zinc electroplating bath

All electroplating baths were cleaned after mixing the ingredients with zinc dust.

2a. Acidic zinc electroplating bath containing ammonia

| | |
|---|---|
| zinc chloride | 90 g/l |
| ammonium chloride | 160 g/l |
| pH | 4.9-5.8 |
| compound. of Ex. 1 (n = 24) | 6 g/l |
| sodium benzoate | 3 g/l |
| benzylidene icetone | 0.2 g/l |
| Hull-cell | 1 A - 15 min. |
| range of bright depositis | 0.1 to 5 A/dm$^2$ |

2b. acidic zinc electroplating bath, free of ammonia

| | |
|---|---|
| zinc chloride | 90 g/l |
| potassium chloride | 200 g/l |
| boric acid | 25 g/l |
| pH | 4.9-5.8 |
| compound of Ex. 1 (n = 12) | 4 g/l |
| sodium benzoate | 2 g/l |
| benzylidene acetone | 0.1 g/l |
| Hull-cell | 1 A - 15 min. |
| range of bright deposits | 0.1 to 5 A/dm$^2$ |

2c. cyan free zinc electroplating bath

| | |
|---|---|
| zinc oxide | 12.5 g/l |
| sodium hydroxyde | 120 g/l |
| salt of Rochelle | 4 g/l |
| reaction product of dimethyl aminopropyl amine with epichlorohydrin (Molar ratio 2:1) | 1.5 g/l |
| n-benzyl nicotinate | 0.1 g/l |
| compound of Ex. 1 (n = 12) | 0.2 g/l |
| Hull-cell | 1 A - 15 min. |
| range of bright deposits | 0.2 to 7 A/dm$^2$ |

2d. cyanidic zinc electroplating bath

| | low | higher cyanidic |
|---|---|---|
| zinc oxide | 12.5 g/l | 37.5 g/l |
| sodium cyanide | 17.5 g/l | 90 g/l |
| sodium hydroxide | 85 g/l | 50 g/l |
| n-benzyl nicotinate | 0.5 g/l | 0.5 g/l |
| compound of Ex. 1 (n = 6) | 0.1 g/l | 0.2 g/l |
| polyethylene imine (mol weight 2000) | 0.2 g/l | 0.2 g/l |
| Hull-cell | 1 A - 15 min. | |
| range of bright deposits | 0.1 to 5 A/dm$^2$ | 0.3 to 7 A/dm$^2$ |

EXAMPLE 3

| | |
|---|---|
| Nickel electroplating bath | |
| nickel sulfate heptahydrate | 330 g/l |
| nickel chloride hexahydrate | 70 g/l |
| boric acid | 50 g/l |
| pH | 3.5-4.6 |
| pyridinium propyl sulfobetaine | 0.2 g/l |
| Saccharin | 4 g/l |
| Propargyl alcohol | 0.1-0,1 g/l |
| compound of Ex. 1 (n = 24) | 0.4 g/l |
| Hull-cell | 2 A - 10 min. |
| temperature | 60° C. |

EXAMPLE 4

| | |
|---|---|
| Zinc/Nickel electroplating bath | |
| zinc chloride | 100 g/l |
| nickel chloride hexahydrate | 130 g/l |
| ammonium chloride | 200 g/l |
| compound of Ex. 1 (n = 15) | 4 g/l |
| benzylidene acetone | 0.1 g/l |
| pH | 5.1-6.1 |
| Hull-cell | 1 A - 15 min. |
| temperature | 35 to 45° C. |
| range of bright deposits | 0.2 to 8 A/dm$^2$ |

EXAMPLE 5

High Performance electroplating baths

| | | |
|---|---|---|
| 5a. | zinc electroplating | |
| | zinc sulfate - heptahydrate | 790 g/l |
| | zinc chloride | 4 g/l |
| | boric acid | 6 g/l |
| | pH | 3 |
| | compound of EX. 1 (n = 12) | 0.1-10 g/l |
| | aluminum sulfate | 24 g/l |
| | current density | to 110 A/dm$^2$ |
| | temperature 60° C. | |

5b. Zinc/Nickel electroplating bath

| | |
|---|---|
| zinc sulfate - heptahydrate | 162 g/l |
| nickel sulfate heptahydrate | 316 g/l |
| naphthalene sulfonic acid | 1 g/l |

| | |
|---|---|
| compound of Ex. 1 (n = 12) | 0.1-2 g/l |
| current density | up to 100 a/dm² |
| temperature | 60° C. |

With all baths bright ductile deposits were obtained which were resistant to wiping and abrasion.

EXAMPLE 6

Acidic ammonium containing zinc electroplating bath

| | |
|---|---|
| zinc chloride | 90 g/l |
| ammonium chloride | 160 g/l |
| potassium-2-naphthyl-(polypropylenglycol)$_{2,5}$ (polyethylenglycol)$_8$-3-sulfopropyl diether (prepared according to Ex. 1) | 6 g/l |
| sodium benzoate | 3 g/l |
| benzylidene acetone | 0.2 g/l |
| Hull-cell | 1 A - 15 min. |
| range of bright deposits | 0.1 to 5 A/dm² |

EXAMPLE 7

Acidic ammoniumfree zinc electroplating bath

| | |
|---|---|
| zinc chloride | 90 g/l |
| potassium chloride | 200 g/l |
| boric acid | 25 g/l |
| pH | 4.9-5.8 |
| potassium-2-napthyl-(polypropylene glycol)$_{2,5}$ (polyethylen glycol)$_8$-3-sulfopropyl diether (prepared according to Ex 1.) | 4 g/l |
| sodium benzoate | 4 g/l |
| benzylidene acetone | 2 g/l |
| Hull-cell | 0,1 g/l |
| range of bright deposits | 1 A - 15 min. |
| | 0.1 to 5 A dm² |

EXAMPLE 8

Cyanfree zinc electroplating bath

| | |
|---|---|
| zinc oxide | 12.5 g/l |
| sodium hydroxide | 120 g/l |
| salt of Rochelle | 4 g/l |
| reaction product of Dimethylaminopropylamine with epichlorohydrin (molar ratio 2:1) | 1.5 g/l |
| n-benzyl nicotinate | 0.1 g/l |
| potassium-2-naphthyl-(polypropylene glycol)$_{2,5}$ (polyethyleglycol)$_8$-3-sulfopropyl diether (prepared according to Ex. 1) | |
| Hull cell | 1 A - 15 min. |
| range of bright deposits | 0.2 to 7 A/dm² |

We claim:

1. A polyalkyleneglycol naphthyl-3-sulfopropyl diether compound, or salt thereof, of the formula:

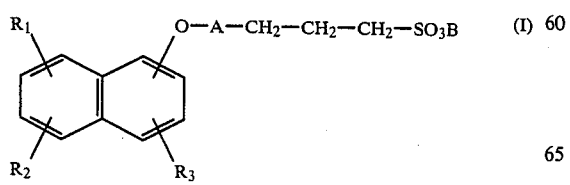

wherein, $R_1$, $R_2$ and $R_3$ represent a member selected from the group consisting of hydrogen and a lower alkyl group $C_pH_{2p+1}$ wherein p is an integer from 1 to 4;

A represents a member selected from the group consisting of $-(PO)_m-(EO)_n-$, $-(EO)_n-(PO)_m-$ and $-(EO)(PO)_n$, wherein EO is a $-CH_2CH_2-O-$ group and PO is a member selected from the group consisting of

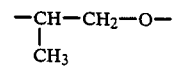

and

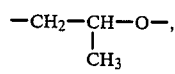

m is an integer of from 0 to 15, and n is an integer from 1 to 40; and,

B is a member selected from the group consisting of hydrogen, an alkali metal, an earth alkali metal and an ammonium cation of the formula $NR_4R_5R_6R_7$ wherein $R_4$-$R_7$ are independently selected from the group consisting of hydrogen, an alkyl group of from 1 to 4 carbon atoms, an aryl and an aralkyl group.

2. A process for the preparation of a polyalkyleneglycol naphthyl-3-sulfopropyl diether compound, or a salt thereof, of the formula:

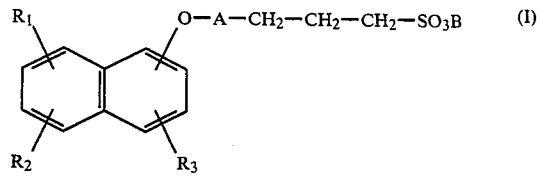

wherein, $R_1$, $R_2$ and $R_3$ represent a member selected from the group consisting of hydrogen and a lower alkyl group $C_pH_{2p+1}$ wherein p is an integer from 1 to 4;

A represents a member selected from the group consisting of $-(PO)_m-(EO)_n-$, $-(EO)_n-(PO)_m-$ and $-(EO)(PO)_n$, wherein EO is a $-CH_2CH_2-O-$ group and PO is a member selected from the group consisting of

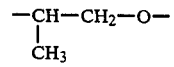

and

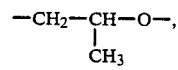

m is an integer of from 0 to 15, and n is an integer from 1 to 40; and,

B is a member selected from the group consisting of hydrogen, an alkali metal, an earth alkali metal and an ammonium cation of the formula $NR_4R_5R_6R_7$ wherein $R_4$-$R_7$ are independently selected from the group consisting of hydrogen, an alkyl group of from 1 to 4 carbon atoms, an aryl and an aralkyl group.
comprising the step of:
reacting a compound of the formula: formula II:

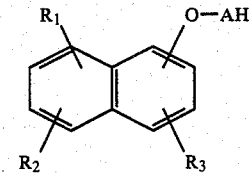

wherein, $R_1$, $R_2$ and $R_3$ represent a member selected from a group consisting of hydrongen and a lower alkyl group $C_pH_{2p+1}$ wherein p is an integer from 1 to 4; and
A represents a member selected from the group consisting of $-(PO)_m-(EO)_n-$, $-(EO)_n-(PO)_m-$ and $-(EO)(PO)_n$, wherein EO is a $-CH_2CH_2-O-$ group and PO is a member selected from the group consisting of

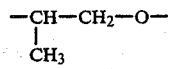

and

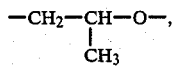

m is an integer of from 0 to 15, and n is an integer from 1 to 40, with propane-1,3-sultone in the presence of a member selected from the group consisting of an alkali hydroxide, an earth alkali hydroxide and ammonium hydroxide of the formula $NR_4R_5R_6R_7OH$, wherein $R_4-R_7$ are independently selected from the group consisting of an alkyl group of from 1 to 4 carbon atoms, an aryl and an aralkyl group.

3. The process according to claim 2, further comprising the step of replacing B of the compound obtained with hydrogen.

4. The process according to claim 3, further comprising the step of neutralizing an acid obtained with a base of the formula $NR_4R_5R_6R_7$.

5. An electroplating bath or an electroless chromium plating bath comprising at least one polyalkyleneglycol naphthyl-3-sulfopropyl diether compound, or a salt thereof, of the formula:

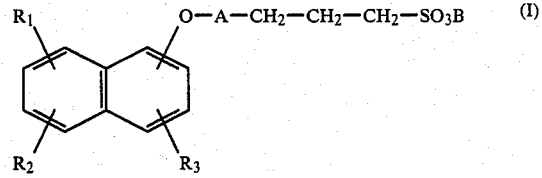

wherein, $R_1$, $R_2$ and $R_3$ represent a member selected from a group consisting of hydrogen and a lower alkyl group $C_pH_{2p+1}$ wherein p is an integer from 1 to 4;
A represents a member selected from the group consisting of $-(PO)_m-(EO)_n-$, $-(EO)_n-(PO)_m-$ and $-(EO)(PO)_n$, wherein EO is a $-CH_2CH_2-O-$ group and PO is a member selected from the group consisting of

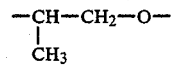

and

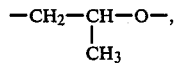

m is an integer of from 0 to 15, and n is an integer from 1 to 40; and,
B is a member selected from the group consisting of hydrogen, an alakli metal, an earth alkali metal and an ammonium cation of the formula $NR_4R_5R_6R_7$ wherein $R_4-R_7$ are independently selected from the group consisting of hydrogen, an alkyl group of from 1 to 4 carbon atoms, an aryl and an aralkyl group.

6. An electroplating bath according to claim 5 for depositing zinc, tin, nickel, copper, silver and alloys thereof wherein m is an integer of from 1 to 5 and n is an integer from 2-24 in defining said compound.

7. An electroless chromium plating bath according to claim 5 wherein m is an integer of from 1 to 5 and n is an integer from 2-24 in defining said compound.

* * * * *